US006879167B2

(12) United States Patent
Ju et al.

(10) Patent No.: US 6,879,167 B2
(45) Date of Patent: Apr. 12, 2005

(54) NONCONTACT MEASURING SYSTEM FOR ELECTRICAL CONDUCTIVITY

(75) Inventors: Yang Ju, Sendai (JP); Masumi Saka, Sendai (JP); Hiroyuki Abe, Sendai (JP)

(73) Assignee: Tohoku Techno Arch Co., Ltd. (JP)

( * ) Notice: Subject to any disclaimer, the term of this patent is extended or adjusted under 35 U.S.C. 154(b) by 0 days.

(21) Appl. No.: 10/441,552

(22) Filed: May 20, 2003

(65) Prior Publication Data

US 2004/0100280 A1 May 27, 2004

(30) Foreign Application Priority Data

Nov. 27, 2002 (JP) ........................................ 2002-343833

(51) Int. Cl.$^7$ .................... G01R 27/04; G01R 27/32
(52) U.S. Cl. ..................................... 324/642; 324/637
(58) Field of Search .................... 324/642, 637, 324/629, 600, 71.1, 250, 158.1, 750, 752, 754, 765, 766, 767, 76.14, 76.56; 438/10, 13, 17, 139; 356/237.4, 237.5

(56) References Cited

U.S. PATENT DOCUMENTS

| | | | | |
|---|---|---|---|---|
| 4,158,165 A | * | 6/1979 | Coates .......................... | 324/338 |
| 4,609,873 A | * | 9/1986 | Cox et al. ..................... | 324/338 |
| 4,893,932 A | * | 1/1990 | Knollenberg ................ | 356/369 |
| 5,049,816 A | * | 9/1991 | Moslehi ........................ | 324/767 |
| 5,197,105 A | * | 3/1993 | Uemura et al. ............... | 382/147 |
| 5,417,494 A | * | 5/1995 | Kempa et al. ................. | 374/5 |
| 5,867,806 A | * | 2/1999 | Strickland et al. ............ | 702/7 |
| 6,562,079 B1 | * | 5/2003 | Takamatsu ..................... | 1/1 |
| 6,674,292 B1 | * | 1/2004 | Bray et al. ..................... | 324/637 |
| 6,701,783 B1 | * | 3/2004 | Fehrenbach et al. .......... | 73/290 V |
| 2002/0011852 A1 | * | 1/2002 | Mandelis et al. ............... | 324/752 |

FOREIGN PATENT DOCUMENTS

JP 02072646 A * 3/1990 ........... H01L/21/66

OTHER PUBLICATIONS

"Accurate Method for the Determination of Bulk Minority–Carrier Lifetimes of Mono–and Multicrystalline Silicon Wafers" Schmidt et al., *J. Appl. Phys.*, 81 (9), May 1, 1997, pp. 6186–6199.

"GaAs Wafer Mapping by Microwave–Detected Photoconductivity" Niklas et al., *Materials Science and Engineering*, B80, vol. 80, No. 1–3, 2001, pp. 206–209.

"Frequency Scaling of Microwave Conductivity in the Integer Quantum Hall Effect Minima" Lewis et al., *Physical Review B* vol. 64, 2001, pp. 073310–1–073310–4.

Preliminary Program, JSNDI Spring Conference 2002, May 28–29, 2002 in Tokyo, Japan, Proceedings of the 2002 Annual Meeting of Japan Society of Mechanical Engineers/MDD, Oct. 12–114, 2002 in Tokyo, Japan.

Ju, et al. "Contactless measurement of electrical conductivity of semiconductor wafers using the reflection of millimeter waves", Applied Physics Letters, vol. 81, No. 19, Nov. 4, 2002,.

* cited by examiner

*Primary Examiner*—Anjan Deb
*Assistant Examiner*—Hoai-An D. Nguyen
(74) *Attorney, Agent, or Firm*—Hayes Soloway P.C.

(57) ABSTRACT

The invention provides a noncontact measuring system for electrical conductivity, which uses a microwave. In the measuring system for electrical conductivity, the microwave generated in a network analyzer (NA) 110 is guided to a surface of a silicon wafer (sample) 160 through a waveguide 130 and a sensor 140. The surface of the silicon wafer 160 is irradiated with the microwave, and the sensor 140 receives the reflected microwave. The electrical conductivity of the silicon wafer 160 is measured in such a manner that a computer (personal computer) 120 calculates the electrical conductivity from an amplitude ratio A and phase difference θ to a reflected wave of the silicon wafer 160, which is determined with the network analyzer 110. The computer 120 performs not only the calculation of the measurement but also whole control of the measuring system such as positioning of the sample.

4 Claims, 7 Drawing Sheets

NONCONTACT MEASURING SYSTEM FOR ELECTRICAL CONDUCTIVITY

BACKGROUND OF THE INVENTION

1. Field of the Invention

The present invention relates to an electrical conductivity measuring system for a material, particularly relates to the electrical conductivity measuring system on a noncontact basis, in which a microwave is used.

2. Description of the Prior Art

Measurement of the electrical conductivity is essential in quality control and performance evaluation of a silicon wafer which is a typical material used for electronic devices.

A four-point probe method is conventionally adopted as the measuring method for the electrical conductivity of the silicon wafer. Though the four-point probe method has an advantage of the quite easy measurement, there is a problem that a leading end of the probe hurts a surface of the wafer because it is necessary that the leading end of the probe is in contact with the wafer during the measurement. Calibration of a thickness of the wafer is also required in quantitative evaluation. Therefore, the four-point probe method can not be adopted for on-line inspection in a manufacturing process of the silicon wafer or non-destructive inspection prior to the manufacturing of the device, and a spot check of few pieces of the silicon wafer products is the only way to inspect the silicon wafer.

The noncontact measuring method for the electrical conductivity is required to realize the non-destructive inspection. In the noncontact measuring method for the electrical conductivity, there is a technique in which a coil is used. However, a change in impedance of an induction coil depends on not only the electrical conductivity of the wafer but also permittivity and the thickness of the wafer. Accordingly, an additional measurement, e.g. the measurement in which the thickness of the wafer is determined by other technique is required in the quantitative evaluation of the electrical conductivity in which the coil is used. The technique using the coil also has the problem of low spatial resolution, so that it is not suited for the non-destructive inspection of the wafer prior to the manufacturing of the device.

In recent years, a study concerning the non-destructive evaluation of the semiconductor wafer using the microwave receives attention as the new measuring method on a non-contact basis. The measurement of a lifetime of a minority carrier (see non-patent reference 1) has been realized, and the evaluation of photoconductivity of the wafer (see non-patent reference 2) and dependence on the electrical conductivity of an absorption peak of the microwave (see non-patent reference 3) have been also reported.

However, the quantitative evaluation of the electrical conductivity of the semiconductor wafer has not been successful yet due to influence of the permittivity and thickness of the wafer, or the like.

(Non-Patent Reference 1)
J. Schmidt and A. G. Aberle: Accurate Method for the Determination of Bulk Minority-Carrier Lifetimes of Mono- and Multicrystalline Silicon Wafers, Journal of Applied Physics, Vol. 81, No. 9, pp. 6186–6199, (1997)

(Non-Patent Reference 2)
J. R. Niklas, W. Siegel, M. Jurisch and U. Kretzer: GaAs Wafer Mapping by Microwave-Detected Photoconductivity, Materials Science and Engineering B, Vol. 80, No. 1–3, pp. 206–209, (2001).

(Non-Patent Reference 3)
R. M. Lewis and J. P. Carini: Frequency Scaling of Microwave Conductivity in the Integer Quantum Hall Effect Minima, Physical Review B, Vol. 64, No. 7, 073310, (2001).

SUMMARY OF THE INVENTION

It is an object of the invention to provide an electrical conductivity measuring system on a noncontact basis, in which the microwave is used.

In order to achieve the above-described object, the invention is the noncontact measuring system for the electrical conductivity characterized by including microwave transmitting/receiving means which transmits and receives the microwave, measuring means which measures an amplitude ratio of the transmitted microwave and a received reflected-wave, and electrical conductivity calculating means which determines the electrical conductivity of a low frequency from the measured amplitude ratio.

Further, the invention is the noncontact measuring system for the electrical conductivity characterized by including microwave transmitting/receiving means which transmits and receives the microwave, measuring means which measures an amplitude ratio and phase difference of the transmitted microwave and a received reflected-wave, electrical conductivity calculating means which determines the apparent electrical conductivity from the measured amplitude ratio and phase difference, and electrical conductivity calibration means which determines the electrical conductivity of the low frequency from the determined apparent electrical conductivity.

DETAILED DESCRIPTION OF THE INVENTION

Preferred embodiments of the invention will be described referring the accompanying drawing.

Figure 1:
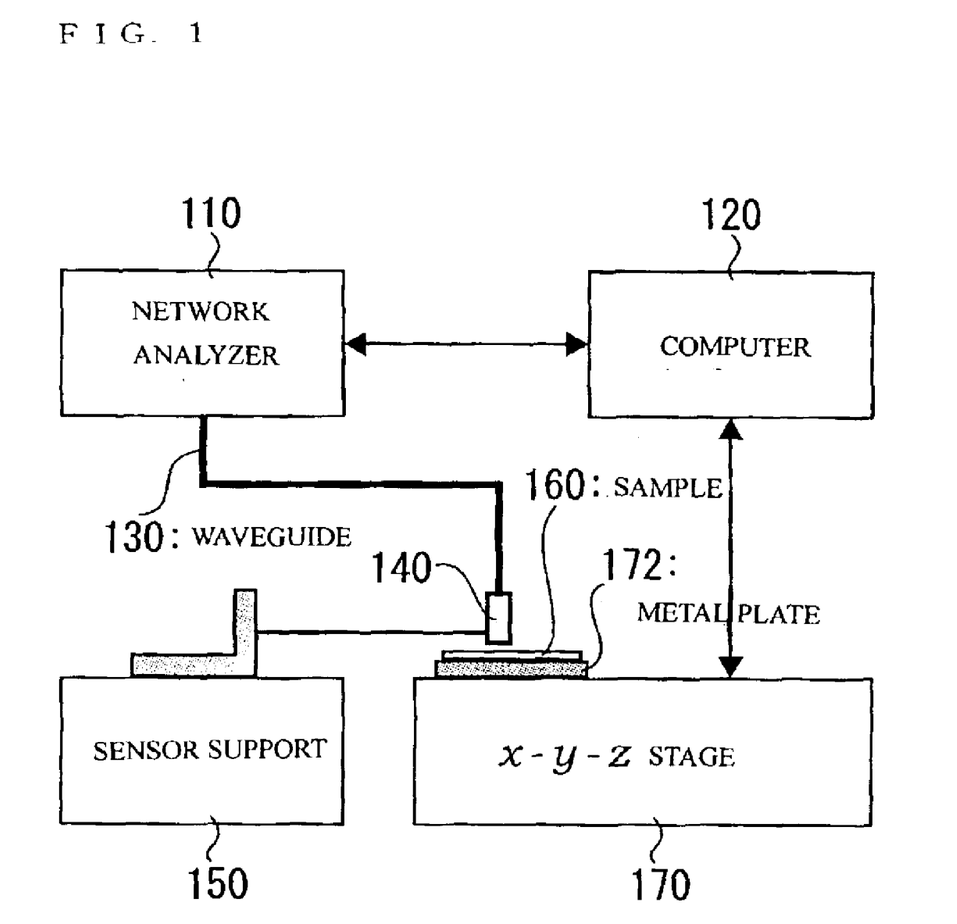
FIG. 1 shows an example of a configuration of the electrical conductivity measuring system.

FIG. 1 shows the configuration of the electrical conductivity measuring system using the microwave according to the embodiment of the invention. The measuring system includes a network analyzer (NA) 110, a computer (personal computer) 120, a waveguide 130, a sensor 140, and an x-y-z stage 170. The microwave generated in the network analyzer 110 is guided to the surface of a silicon wafer (sample) 160 through the waveguide 130 and the sensor 140. The surface of the silicon wafer 160 is irradiated with the microwave, and the sensor 140 receives the reflected microwave. The electrical conductivity of the silicon wafer 160 is measured in such a manner that the computer 120 calculates the electrical conductivity from an amplitude ratio A and phase difference θ to the reflected wave of the silicon wafer 160, which is determined with the network analyzer 110.

The sensor 140 positions the sample 160 by relative motion between a sensor support 150 and the x-y-z stage 170. The computer 120 performs not only the calculation of the measurement but also whole control of the measuring system such as the positioning of the sample. Though the network analyzer is used for measurement of the amplitude ratio and phase difference of the microwave in the above-described measuring system, it is not limited to the network analyzer.

Figure 2:
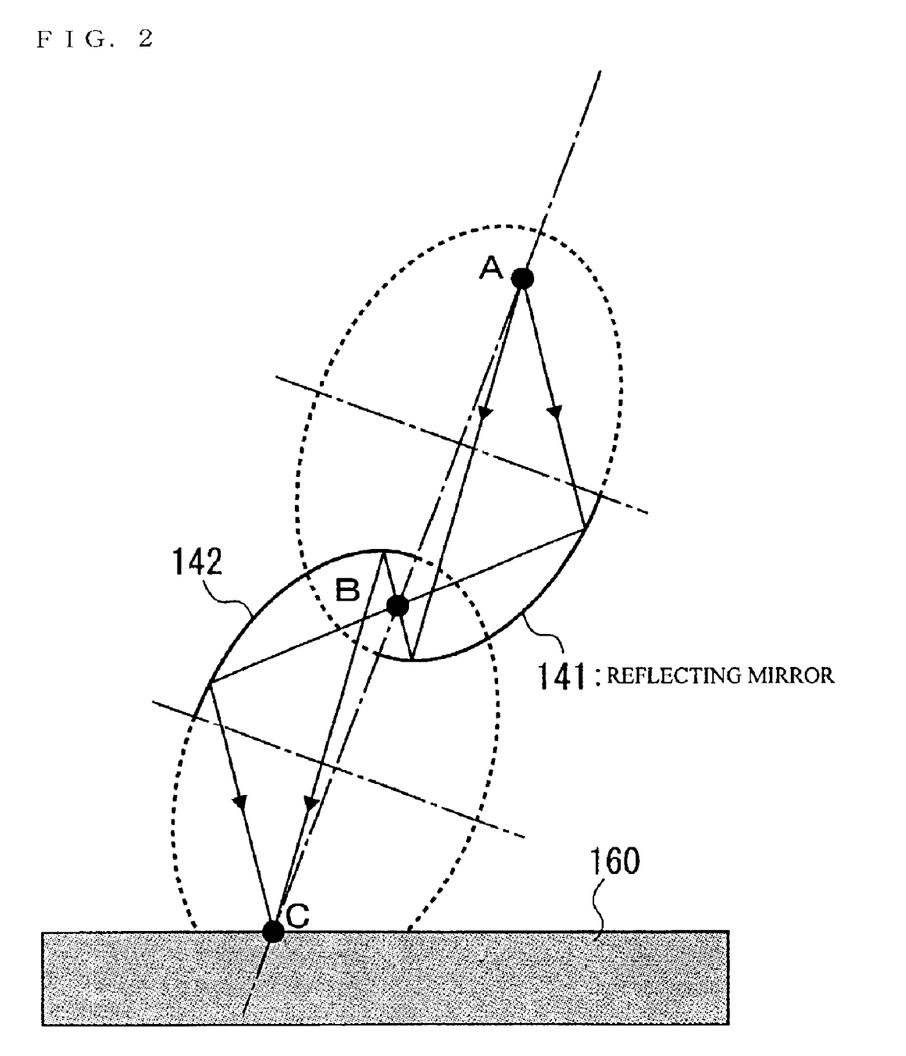
FIG. 2 shows the configuration of a reflective type of microwave converging sensor which is used in the electrical conductivity measuring system.

FIG. 2 shows the configuration of the reflective type of microwave converging sensor which is developed.

A shape of reflecting mirrors 141 and 142 of the used microwave is an ellipsoidal plane. In the optics, when a light source is placed at one focal point A in the ellipsoid, incident light is reflected on the ellipsoidal plane and condensed at the other focal point B. Further, the phases are coherent because an optical path from the focal point A to the focal point B is constant. In the embodiment of the invention, by adopting this principle, the two reflecting mirrors 141 and 142 are combined so as to share the focal point B, stand-off distance is formed as much as possible, and the microwave from the focal point A converges into a focal point C.

Actually combination of the reflecting mirrors 141 and 142 (solid line parts in FIG. 2), which is two quarters of the ellipsoid, and a horn antenna (not shown) are integrally fixed, and it is used as one sensor 140.

By using the sensor 140, a minuter region can be irradiated with the converged microwave compared with the conventional non-convergence sensor, so that silicon wafer can be evaluated on a non-destructive basis with a larger stand-off distance, higher resolution, and higher sensitivity.

Though FIG. 2 shows the example of the reflective type of microwave converging sensor in which the two reflecting mirrors having the ellipsoidal plane are combined, three or more reflecting mirrors may be combined in the same way.

<PRINCIPLE OF MEASUREMENT>

In the above-described system, the microwave to be used is an electromagnetic wave having a frequency of 300 MHz to 300 GHz (wavelength of 1 m to 1 mm). Because the microwave propagates through the air without a transmitter medium, the material can be evaluated on noncontact and non-destructive bases with the microwave. Further, because response of the microwave depends on the permittivity, permeability, and the electrical conductivity of the material, the change in the material can be measured with high sensitivity.

The reflection measuring method using the microwave is adopted in the measuring system of the invention. This is the method in which the material is irradiated with the microwave and the amplitude and the phase of the reflectivity, which is the ratio of the reflected wave to the incident wave, are measured.

Suppose that an angular frequency of the microwave is ω, the permeability of the material is μ, the permittivity of the material is ε, and the electrical conductivity is σ, characteristic impedance η of the material and characteristic impedance $\eta_o$ in the air are determined by the following equations.

[EQUATION 1]

$$\eta = \sqrt{\frac{\mu}{\varepsilon - j\frac{\sigma}{\omega}}} \quad (1)$$

$$\eta_o = \sqrt{\frac{\mu_o}{\varepsilon_o}} \quad (2)$$

Where $\mu_o$ and $\varepsilon_o$ indicate permeability of vacuum magnetic constant and permittivity of vacuum electric constant respectively. The reflectivity $\Gamma_t$ on the surface of the material can be represented by the following equation.

[EQUATION 2]

$$\Gamma_t = \frac{\eta - \eta_o}{\eta + \eta_o} \quad (3)$$

When the silicon wafer is irradiated with the high-frequency microwave, a component of the microwave transmitted by the surface of the wafer is largely attenuated inside the silicon wafer. When terms of the electrical conductivity and thickness of the wafer satisfy given conditions, the amount of microwave reflected from a bottom surface of the wafer to the sensor is as small as negligible. For example, when the microwave having the frequency of 110 GHz is used, the reflectivity of the microwave reflected from the bottom surface of the silicon wafer having the thickness of 500 μm and the electrical conductivity of 200 S/m becomes about $1/10^4$ of $\Gamma_t$. Accordingly, only $\Gamma_t$ on the surface of the material may be taken into consideration.

In the measurement concerning the silicon wafer, the wafer is a non-magnetic material, by substituting equations (1) and (2) for the equation (3), $\Gamma_t$ can be expressed as follows.

[EQUATION 3]

$$\Gamma_t = a + jb = \frac{1 - \sqrt{\frac{\varepsilon}{\varepsilon_o} - j\frac{\sigma}{\omega \varepsilon_o}}}{1 + \sqrt{\frac{\varepsilon}{\varepsilon_o} - j\frac{\sigma}{\omega \varepsilon_o}}} \quad (4)$$

The reflectivity $\Gamma_t$ is a complex number, its real part is set to a and its imaginary part is set to b. $\omega$ is constant on the right side of the equation (4). Therefore, when $\varepsilon$ is eliminated from the expression of the real part and the imaginary part of the equation (4), $\sigma$ is derived as shown in the following equation (5), and $\sigma$ becomes a function having variables a and b. As a result, the electrical conductivity of the wafer and the response of the microwave can be derived by a one-to-one relational expression.

[EQUATION 4]

$$\sigma = \frac{4\omega \varepsilon_o b(1 - a^2 - b^2)}{\{(1+a)^2 + b^2\}^2} \quad (5)$$

<CONCRETE EXAMPLE>

The n-type of silicon wafer having a plane direction <100> was used as a test piece. In a size of the wafer, a diameter was 100 mm and the thickness was 525 μm. Three groups of the wafer, which have the electrical conductivity of 9 to 11, 50 to 110, and 166 to 333 S/m respectively, were used. The reflective type of microwave converging sensor shown in FIG. 2 was used and the stand-off distance between the sensor and the test piece was constantly set to 35 mm. The frequency was set to 110 GHz, the amplitude ratio A and the phase difference θ of the microwave which was transmitted and received were measured. Paying attention to temperature dependence of the electrical conductivity in the measurement, all the measurements were performed under the condition of a room temperature of 21° C.

Substituting the amplitude ratio A and the phase difference θ of the microwave which was transmitted and received for the following equation, the reflectivity $\Gamma_m$ of the microwave was determined from the measurement.

[EQUATION 5]

$$\Gamma_m = 10^{\frac{A}{20}} * e^{j\theta} \quad (6)$$

$\sigma_m$ by the microwave measurement was determined by substituting a real part am and an imaginary part $b_m$ of $\Gamma_m$ for the equation (5). Where $\sigma_m$ is the apparent electrical conductivity, and $\sigma_m$ includes an error caused by the measuring apparatus and the sensor and influence of the high frequency. The calibration is required to remove the error and the influence.

At this point, the electrical conductivity of the wafer test piece is measured by the four-point probe method and its value is set to $\sigma_d$. Comparing $\sigma_m$ obtained by the microwave to $\sigma_d$ obtained by the four-point probe method, a calibration equation is derived. By adopting the calibration equation, the electrical conductivity $\sigma_l$ for the low frequency of the test piece can be measured with the microwave.

Figure 3:
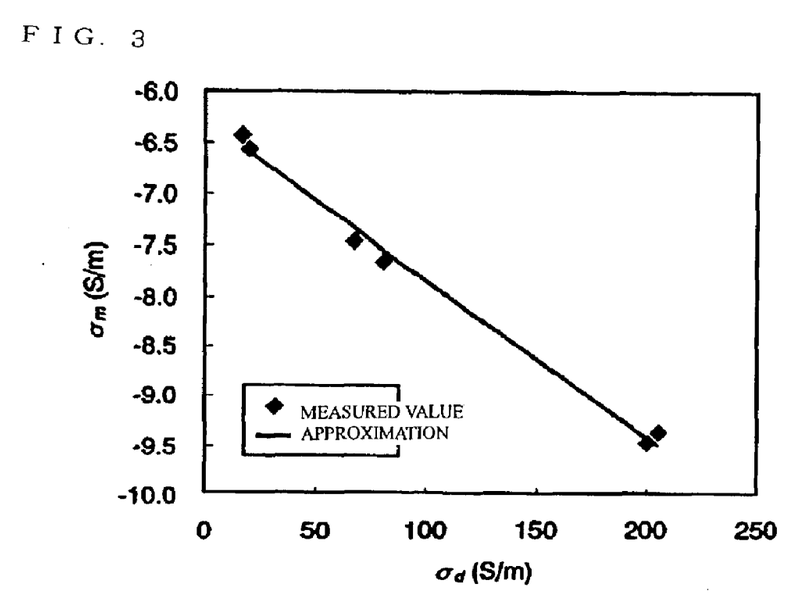
FIG. 3 is a graph showing a relationship between apparent electrical conductivity $\sigma_m$ and electrical conductivity $\sigma_d$ which is obtained by a four-point probe method.

In order to derive the calibration equation, the test pieces of each group were measured by the noncontact measuring method using the microwave and the four-point probe method. FIG. 3 shows the apparent electrical conductivity $\sigma_m$ obtained by the noncontact measuring method using the microwave and electrical conductivity $\sigma_d$ obtained by the four-point probe method.

From the result shown in FIG. 3, the following calibration equation was obtained by replacing $\sigma_d$ by the electrical conductivity $\sigma_l$ for the low frequency.

[EQUATION 6]

$$\sigma_l = C_1 \sigma_m + C_2 \quad (7)$$

Where $C_1 = -63.69$ and $C_2 = -400.63$ S/m. By adopting the calibration equation (7), the electrical conductivity $\sigma_l$ for the low frequency can be determined by the noncontact measuring method using the microwave.

Figure 4:
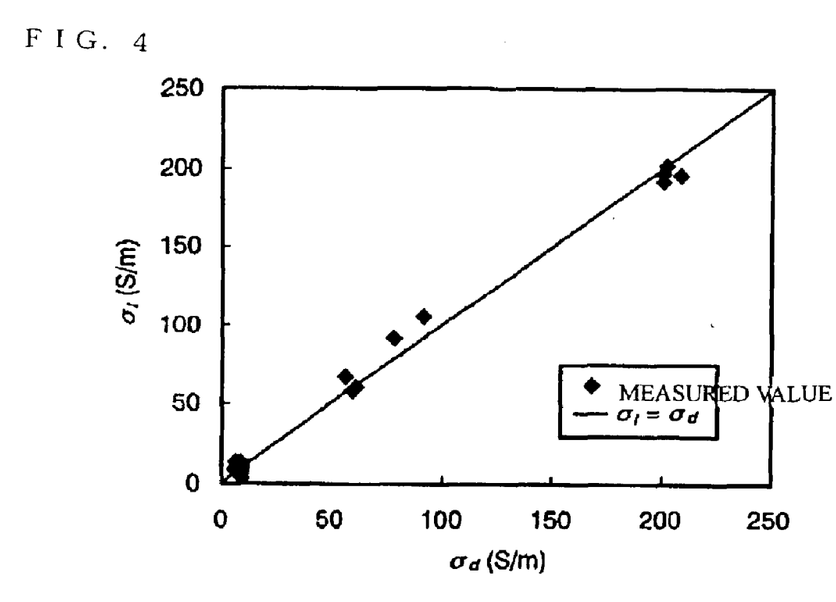
FIG. 4 is a graph showing the relationship between the calibrated electrical conductivity $\sigma_d$ for a low frequency and the electrical conductivity $\sigma_l$ which is obtained by the four-point probe method.

FIG. 4 is a graph showing comparison between the electrical conductivity, in which the apparent electrical conductivity $\sigma_m$ obtained by the noncontact measuring method using the microwave is calibrated to the electrical conductivity $\sigma_l$ for the low frequency with the calibration equation (7), and the electrical conductivity σd obtained by the four-point probe method.

As shown in FIG. 4, the electrical conductivity $\sigma_l$ obtained by the noncontact measuring method using the microwave well conforms to the electrical conductivity $\sigma_d$ measured by the four-point probe method.

When the measuring condition or a kind of the wafer is changed, since $C_1$ and $C_2$ of the calibration equation are also changed, it is necessary to determine $C_1$ and $C_2$. It can be easily obtained in a manner that measures two reference samples by the noncontact measuring method using the microwave and the four-point probe method.

Though the calibration equation shows the linear equation in the above-described embodiment, since the calibration equation is the relationship between the electrical conductivity obtained by the noncontact measuring method using the microwave and the electrical conductivity obtained by the four-point probe method, it is not limited to the linear equation.

As described above, by adopting the measuring system, when the wafer has the thickness in which the reflected wave from the bottom surface of the wafer can be negligible, the electrical conductivity of the semiconductor wafer can be measured on a noncontact basis without depending on the carrier type.

When σ is eliminated from the equation (4) of the real part and imaginary part, $\varepsilon$ is derived as shown below and becomes the function having the variables a and b. This also allows the permittivity of the semiconductor wafer to be measured on a noncontact basis from the response of the microwave, similarly to the above-described way.

[EQUATION 7]

$$\varepsilon = \frac{(a^2 + b^2 - 1)^2 - 4b^2}{\{(1+a)^2 + b^2\}^2} \varepsilon_o$$

<ANOTHER EMBODIMENTS>

Figure 5:
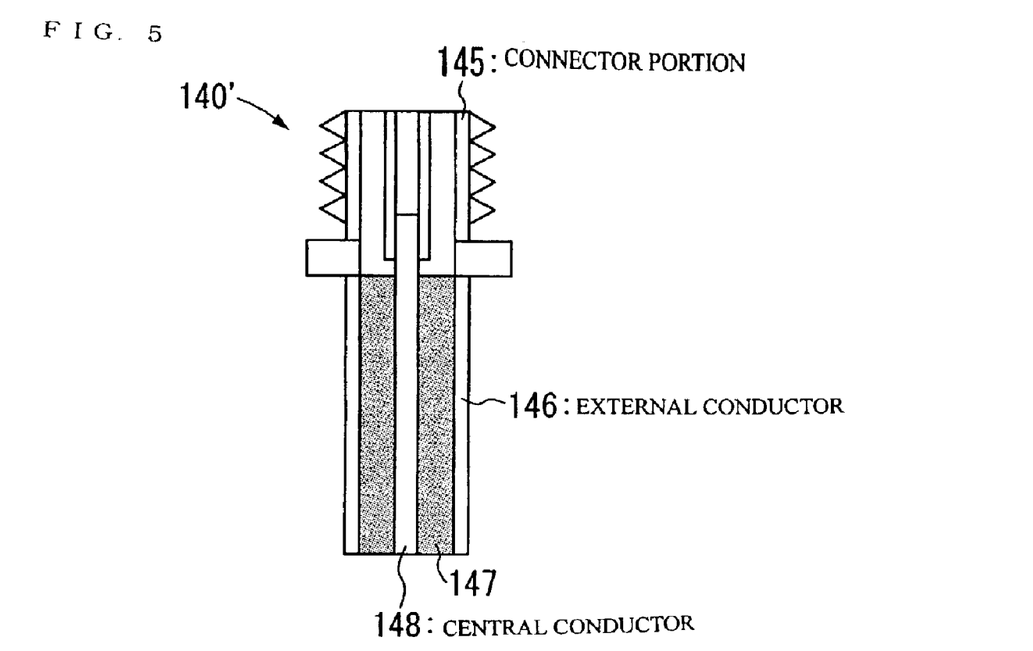
FIG. 5 shows a construction of a coaxial cable sensor which is used in the electrical conductivity measuring system.

In the measuring system having the same configuration as that of FIG. 1, the electrical conductivity of the semiconductor wafer can be also measured in such a manner that a high-resolution coaxial cable sensor 140' shown in FIG. 5 is used as the sensor and the amplitude of the reflectivity, i.e.

only the amplitude ratio of the transmitted microwave to the received reflected wave is measured.

In the non-destructive evaluation, which uses the microwave, of the material, the waveguide is usually used as the sensor. However, in the waveguide, there is a cutoff frequency indicating the lower limit of the frequency, where the microwave can not be transmitted lower than the frequency. It is necessary to enlarge the size of the waveguide in order to lower the cutoff frequency below the using frequency, which results in the problem that the spatial resolution is decreased. On the other hand, when the coaxial cable sensor which the inventor has developed is used, the cutoff frequency is eliminated, the wider frequency range can be handled, and the spatial resolution can be improved.

The coaxial cable sensor sends the microwave transmitted from a signal source to the test piece and receives the reflected wave from the test piece. FIG. 5 shows a section of the coaxial cable sensor. The sensor includes a coaxial cable portion having an open end and including a central conductor 148 and an external conductor 146, and a coaxial connector 145 connected to the coaxial cable.

<CONCRETE EXAMPLE>

Concretely the measurement was performed by using the n-type of silicon wafer having the diameter of 100 mm and the thickness of 525 μm as the test piece. A radius of the central conductor 148 in the used coaxial cable sensor was 0.15 mm and an inner radius of the external conductor 146 was 0.47 mm.

The average electrical conductivity of the wafer measured by the four-point probe method was 14.73 S/m. The stand-off distance between the sensor and the test piece was constantly set to 200 μm. The frequency was set to 110 GHz, and the amplitude A of the reflectivity was measured. Paying attention to the temperature dependence of the electrical conductivity, all the measurements were performed under the condition of the room temperature of 25° C.

Figure 6:
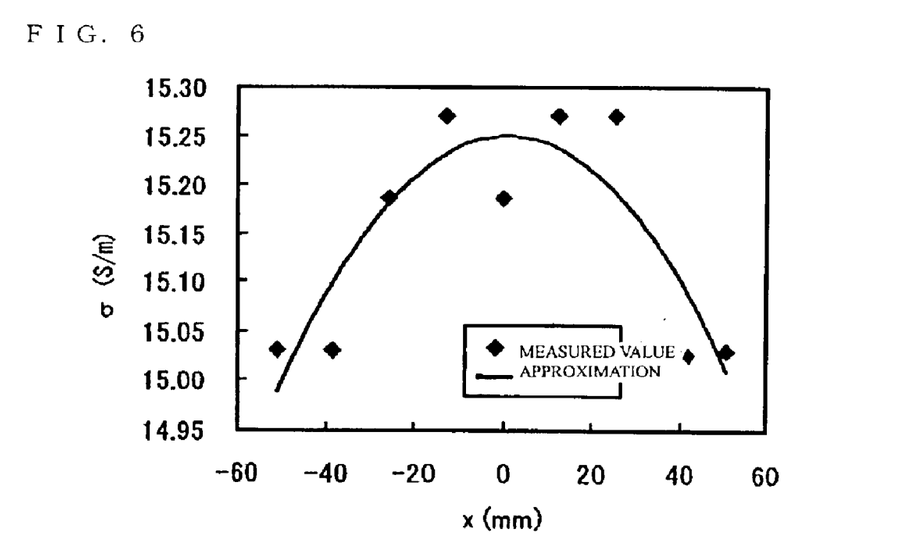
FIG. 6 is a graph showing the electrical conductivity $\sigma$ which is obtained by measuring the silicon wafer of a test piece with the four-point probe method.
Figure 7:
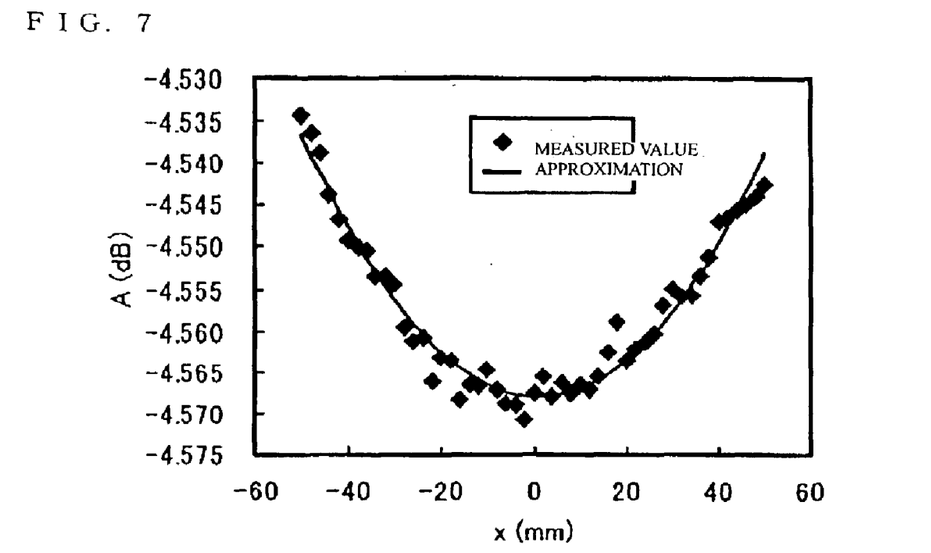
FIG. 7 is a graph showing an amplitude of the reflectivity which is obtained by measuring the silicon wafer of the test piece with the electrical conductivity measuring system.
Figure 8:
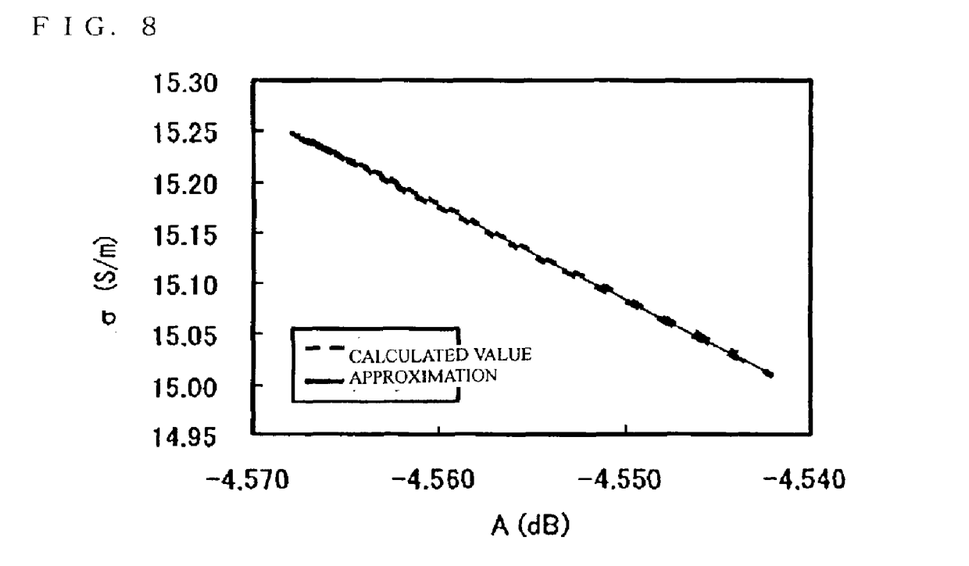
FIG. 8 is a graph showing the relationship between the amplitude of the reflectivity and the electrical conductivity $\sigma$ which is obtained by the four-point probe.

FIG. 6 is the measurement result of the electrical conductivity along a diameter direction of the wafer, which is obtained by the four-point probe method. It is found that the central portion has a slightly larger value compared with the outer portion in the electrical conductivity of the wafer. FIG. 7 is the result measured with the microwave along the same diameter direction as that of FIG. 6. A scanning range is 100 mm and a distance is 2 mm. It is found that the response of the microwave measured from FIG. 7 has the same distribution as that of the electrical conductivity of the wafer shown in FIG. 6. FIG. 8 shows the relationship between the amplitude A of the reflectivity of the microwave and the electrical conductivity of the silicon wafer, which are obtained from FIGS. 6 and 7. The following equation can be obtained from FIG. 8.

[EQUATION 8]

$$\sigma_f = C_1 A + C_2 \quad (8)$$

Where $C_1 = -9.1821$ S/mdB and $C_2 = -26.696$ S/m.

Figure 9:
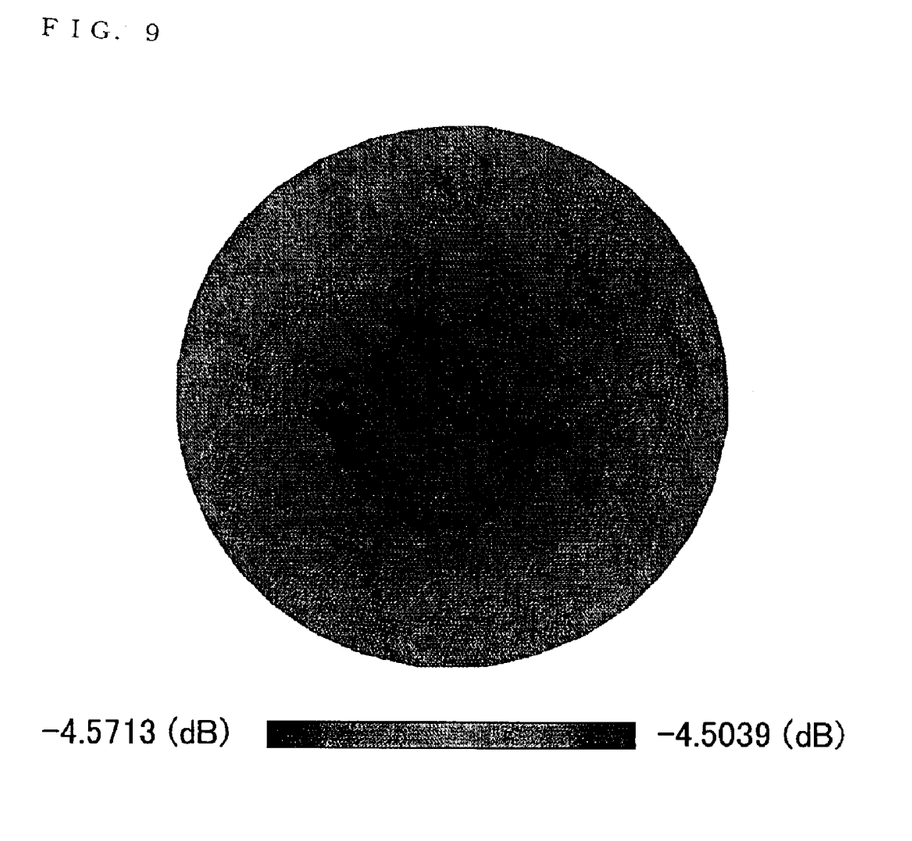
FIG. 9 shows a microwave image depending on magnitude of the reflectivity of the silicon wafer.
Figure 10:
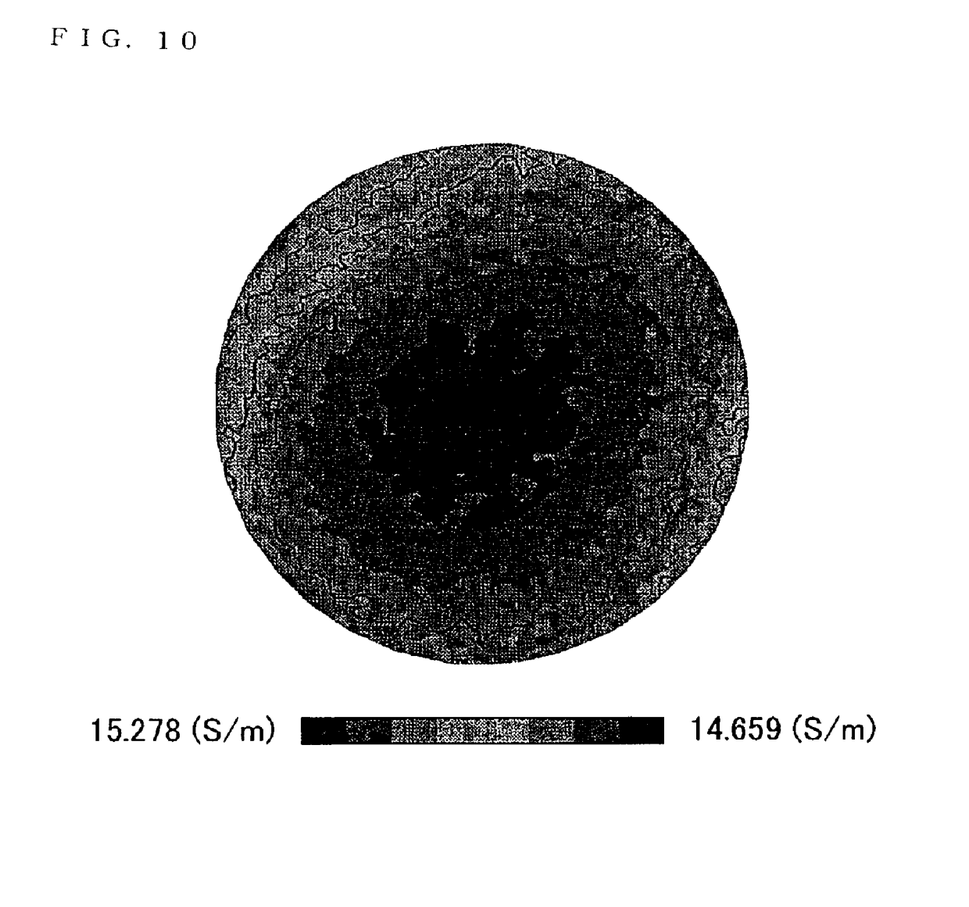
FIG. 10 is a view showing a distribution of the electrical conductivity of the silicon wafer.

FIG. 9 is the microwave image depending on the reflectivity, which is obtained by scanning the silicon wafer while a scanning distance of 2 mm and the diameter of a scanning range is 100 mm in the measuring system of the invention. A two-dimensional distribution map of the electrical conductivity for the silicon wafer, shown in FIG. 10, can be obtained by performing the above-described calculation from FIG. 9. To obtain the precise distribution map of the electrical conductivity shown in FIG. 10 exhibits the high, precise resolution of the electrical conductivity of the measuring system. Though values are color-coded in FIGS. 9 and 10, here the color-coded values are indicated in monochrome.

The reflective type of microwave converging sensor in which the reflecting mirrors of the ellipsoid are combined or the coaxial cable sensor is used in the above-described measuring system, the reflective type of microwave converging sensor has an advantage of enlarging the stand-off distance between the sensor and the wafer, and the coaxial cable sensor has the advantage of the high resolution, so that the using sensor can be selected considering those advantages. The sensor used in the measuring system is not limited to those sensors.

In the concrete example, though the single frequency of 110 GHz was used, other frequencies and multi-frequencies may be used.

The electrical conductivity of the semiconductor or the like can be precisely measured on a noncontact basis by using the above-described electrical conductivity measuring system of the invention.

What is claimed is:

1. A noncontact measuring system for measuring electrical conductivity of a semiconductor wafer comprising:

a microwave transmitter and receiver, including a reflective type of microwave converging antenna, for transmitting microwaves to a minute region of a surface of the semiconductor wafer and for receiving microwaves reflected therefrom;

a reflectivity measurer for measuring reflectivity of a top surface of the semiconductor wafer; and an electrical conductivity sensor for determining electrical conductivity of a low frequency from the measured reflectivity.

2. A noncontact measuring system as defined by claim 1, further comprising:

an electrical conductivity calibrator for creating a two-dimensional distribution map of said electrical conductivity.

3. A noncontact measuring system for measuring electrical conductivity of a semiconductor wafer comprising:

a microwave transmitter and receiver, including a reflective type of microwave converging antenna, for transmitting microwaves to a minute region of a surface of the semiconductor wafer and for receiving microwaves reflected therefrom;

a reflectivity measurer for measuring reflectivity of a top surface of the semiconductor wafer from an amplitude ratio and phase difference of the transmitted and received waves;

an electrical conductivity sensor for determining an apparent electrical conductivity from the measured reflectivity; and an electrical conductivity calibrator for determining electrical conductivity of a low frequency from the determined apparent electrical conductivity.

4. A noncontact measuring system as defined by claim 3, further comprising:

an electrical conductivity calibrator for creating a two-dimensional distribution map of said electrical conductivity.

* * * * *